United States Patent

Buysch et al.

[11] Patent Number: 5,856,554
[45] Date of Patent: *Jan. 5, 1999

[54] PROCESS FOR PRODUCING DIARYL CARBONATES

[75] Inventors: Hans-Josef Buysch; Carsten Hesse, both of Krefeld; Johann Rechner, Kempen, all of Germany

[73] Assignee: Bayer AG, Leverkusen, Germany

[ * ] Notice: The term of this patent shall not extend beyond the expiration date of Pat. No. 5,625,091.

[21] Appl. No.: 853,516

[22] Filed: May 9, 1997

[30] Foreign Application Priority Data

May 17, 1996 [DE] Germany .............................. 19619949.2

[51] Int. Cl.⁶ .................................................. C07C 68/00
[52] U.S. Cl. ............................................................ 558/274
[58] Field of Search .............................. 568/274; 558/274

[56] References Cited

U.S. PATENT DOCUMENTS 5,239,106  8/1993  Schafer ..................................... 558/274
5,625,091  4/1997  Buysch ..................................... 558/274

FOREIGN PATENT DOCUMENTS 583938     2/1994   European Pat. Off. .
28 15 512  10/1979  Germany .

Primary Examiner—Paul J. Killos
Assistant Examiner—Jean F. Vollano
Attorney, Agent, or Firm—Connolly and Hutz

[57] ABSTRACT

The present invention relates to a process for producing diaryl carbonates by the reaction of an aromatic hydroxy compound (e.g. phenol) with carbon monoxide and oxygen in the presence of a catalyst, a co-catalyst, a quaternary salt and a base, which is characterised in that the reaction is conducted in a melt comprising the diaryl carbonate and the hydroxy compound on which the carbonate is based, and further diaryl carbonate is optionally added to this reaction mixture before work-up.

8 Claims, 1 Drawing Sheet

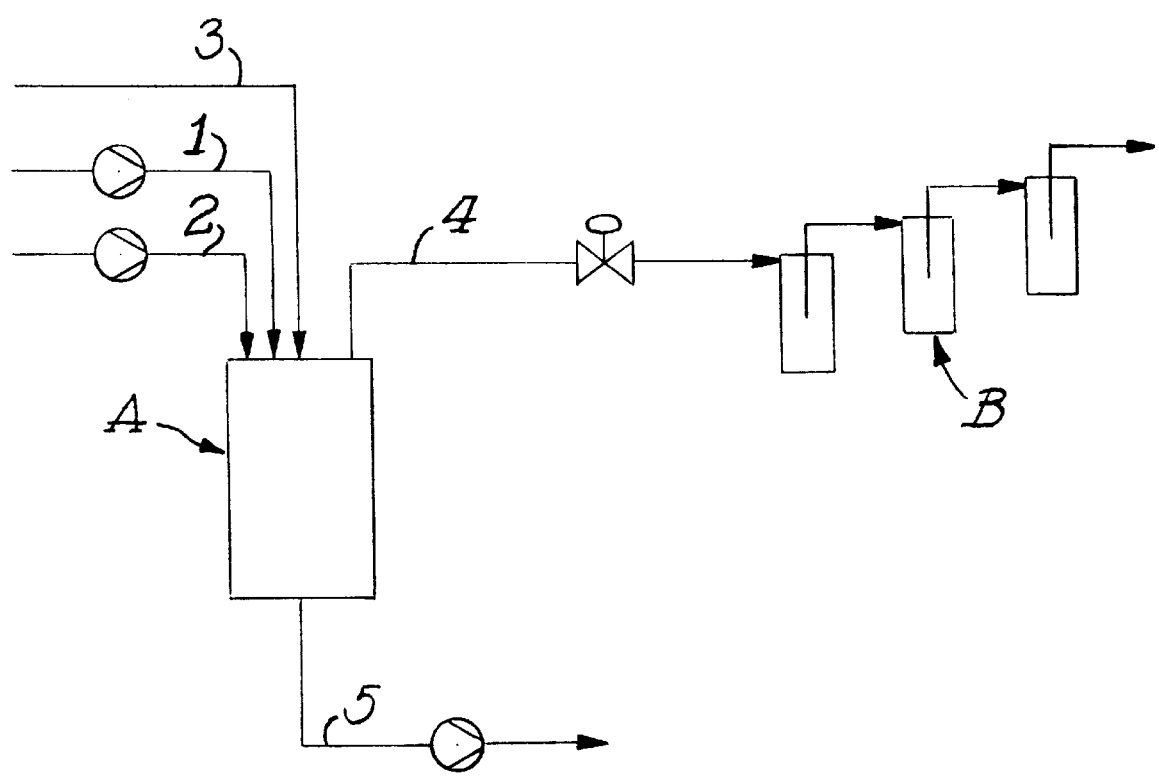

PROCESS FOR PRODUCING DIARYL CARBONATES

The present invention relates to a process for producing diaryl carbonates by the reaction of an aromatic hydroxy compound (e.g. phenol) with carbon monoxide and oxygen in the presence of a catalyst, a co-catalyst, a quaternary salt and a base, which is characterised in that the reaction is conducted in a melt comprising the diaryl carbonate and the hydroxy compound on which the carbonate is based, and further diaryl carbonate is optionally added to this reaction mixture before work-up.

It is known that organic carbonates can be produced by the oxidative reaction of an aromatic hydroxy compound with carbon monoxide in the presence of a noble metal catalyst (DE-A 27 38 437). Palladium is preferably used as the noble metal. In addition, a co-catalyst (e.g. manganese or cobalt salts), a base, a quaternary salt, various quinones or hydroquinones and drying agents can be used. The reaction can also be conducted in a solvent. Methylene chloride is preferably used for this purpose.

The space-time yields achieved with this process are very low and are not acceptable for industrial application. Moreover, the high dilution, the use of molecular sieve and the large amount of catalyst considerably add to the difficulty of work-up, and in addition make this process uneconomic.

Higher diaryl carbonate contents in the reaction solutions are only obtained, if at all, after reaction times of several hours (JP-01 165 551, WO 93/03000, EP-A 583 935, EP-A 583 937 and EP-A 583 938), even though high temperatures and pressures are employed. Long times of reaction result in large reaction volumes and make the process unattractive. Moreover, the addition of a molecular sieve is proposed for the separation of water, in order to prevent the decomposition of the diaryl carbonate formed and to prevent deactivation of the catalyst. The use of molecular sieve makes the industrial utilisation of the process unattractive, since large amounts of molecular sieve are required for the effective separation of the water from the liquid phase (a 100–500% excess is required with respect to the drying capacity and the anticipated amount of water), and have to be regenerated at a high production cost. In the presence of sufficient amounts of molecular sieve, as used in the aforementioned patent applications, the water content in a reaction solution can be limited to a few ppm. The fact that the decomposition of diaryl carbonate is observed despite this suggests that even traces of water result in the rapid decomposition of diaryl carbonate. Consequently, high concentrations of diaryl carbonate in the reaction mixture are therefore also avoided at the same time, in order to suppress the hydrolysis reaction, particularly since it is disclosed in EP-A 583 935 that the reaction proceeds considerably more slowly with increasing diphenyl carbonate concentration in the reaction mixture.

JP-04 257 546 describes a process in which organic carbonates are obtained by the oxidative reaction of an aromatic hydroxy compound with carbon monoxide in the presence of a noble metal catalyst and a quaternary salt, by continuously feeding the reaction mixture into a distillation column at 150°–205° C. and 30–50 bar. The water of reaction is continuously distilled off in the course of this procedure.

A disadvantage of this process is that in order to remove the water of reaction a distillation column has to be employed, which due to its construction only makes short dwell times possible. The space-time yields which can be achieved with this process are accordingly very low, namely only 17.8 g/liter-hour. Conducting the reaction in a distillation column is associated with the use of large amounts of halides at high temperatures (150°–205° C.). This results in considerable corrosion problems, which in addition give rise to high equipment costs. One skilled in the art is also aware that under the given reaction conditions the iodide which is preferably used is not stable and is oxidised to iodine to a significant extent. This results in considerable losses of the quaternary salt and in the formation of by-products, which significantly impair the selectivity and thus the economics of this process. Moreover, at the requisite high temperatures and pressures, a rapid deactivation of the homogeneous catalyst system due to losses of halogen and due to particle growth of the palladium has to be reckoned with, so that it is not possible to utilise this process economically. Furthermore, this process only provides very low diaryl carbonate concentrations and thus has no advantage, as regards the isolation of diaryl carbonate, compared with the processes discussed above. High diaryl carbonate contents are also of course avoided in this process also, in order to reduce losses due to hydrolysis.

A process for the removal of water by stripping with excess reaction gas at 40°–120° C. and 2–50 bar is described in EP-A 667 336.

A disadvantage of this process also is that diaryl carbonate contents higher than 20% by weight can only be obtained after reaction times of several hours. Moreover, this process is of course unsuitable for high diaryl carbonate concentrations, since the removal of water by stripping with excess reaction gas does not have the drying effect of a molecular sieve, and a considerably enhanced hydrolysis reaction is to be expected for this reason.

The isolation from the reaction mixtures of the diaryl carbonate which is formed necessitates a considerable consumption of energy at low contents of diaryl carbonate, since large amounts of solvent or aromatic hydroxy compound have to be separated.

There was therefore a need for a process which permits high diaryl carbonate contents in the reaction mixture to be obtained within short times of reaction, so that the downstream isolation of the diaryl carbonate can be effected with minimal energy consumption.

Surprisingly, it has now been found that the disadvantages of the prior art which were described above can be overcome if the reaction is conducted in a melt comprising diaryl carbonate and the corresponding hydroxy compound, and if high diaryl carbonate contents are thereby already present in the reaction system at the start of the reaction. Even at high contents of diaryl carbonate in the melt, the reaction still proceeds with high space-time yields. Contrary to expectations, hydrolysis reactions or secondary reactions scarcely occur, even at high diaryl carbonate contents. For example, in order to prevent hydrolysis of the diaryl carbonate it is sufficient to remove the water formed in the reaction by stripping with excess reaction gas. The addition of further diaryl carbonate after the reaction is complete can be advantageous for subsequent work-up.

Accordingly, the present invention relates to a process for producing an organic carbonate of formula

R—O—CO—O—R  (I)

wherein
R represents a substituted or unsubstituted $C_6$–$C_{12}$ aryl, preferably a substituted or unsubstituted phenyl, most preferably unsubstituted phenyl,
by the reaction of an aromatic hydroxy compound of formula

(II)

wherein

R has the meaning given above,
with carbon monoxide and oxygen in the presence of a platinum metal catalyst, a co-catalyst, a quaternary salt and a base at a temperature of 30° to 200° C., preferably 30° to 150° C., most preferably 40° to 120° C., and at a pressure of 1 to 200 bar, preferably 2 to 150 bar, most preferably 5 to 75 bar, which is characterised in that the reaction is conducted in a melt comprising a diaryl carbonate and an aromatic hydroxy compound, which at the start of the reaction already has a content of diaryl carbonate of at least 20% by weight, preferably at least 30% by weight, and most preferably at least 40% by weight, and diaryl carbonate is isolated from the melt by methods which are known in principle.

In the process according to the invention, a melt of diaryl carbonate and aromatic hydroxy compound is preferably used which contains 20 to 95% by weight diaryl carbonate, more preferably 30 to 75% by weight diaryl carbonate, most preferably 40 to 60% by weight diaryl carbonate.

In the course of this procedure, diaryl carbonate can be freshly added to the starting material stream of the synthesis reactor or may already be contained in the recycled material stream as a reflux from the diaryl carbonate isolation stage. In the case of a reflux from the diaryl carbonate isolation stage, the desired content of diaryl carbonate then still has to be set if necessary by adding diaryl carbonate after adding the aromatic hydroxy compound. In the process according to the invention, it is not necessary to remove the whole of the diaryl carbonate from the reaction mixture during the isolation of the diaryl carbonate; it is sufficient to remove the diaryl carbonate formed by the reaction.

In a further embodiment, it may be advantageous not to add part of the diaryl carbonate until immediately before the isolation of the diaryl carbonate. It has now been found that it is advantageous if the melt contains at least 40% by weight, preferably at least 45% by weight, most preferably more than 50% by weight of diaryl carbonate before the work-up step. Even in reaction mixtures which have been prepared by other processes which are known in principle, the work-up stage is advantageously influenced by the addition of diaryl carbonate to the melt. The present invention therefore also relates to a method of isolating diaryl carbonate from reaction mixtures containing a diaryl carbonate and an aromatic hydroxy compound, in which an amount of diaryl carbonate is added to the mixture such that the proportion thereof amounts to at least 40% by weight of the reaction mixture, and diaryl carbonate is subsequently isolated from the reaction mixture in a manner which is known in principle.

In the process according to the invention, the removal of the water formed during the reaction can be effected by a molecular sieve, by its removal by distillation from a circulating flow or by stripping with excess reaction gas. The water is preferably removed by stripping with excess reaction gas.

During removal by distillation, part of the reaction mixture is removed, depressurised, and then dewatered substantially isothermally under reduced pressure by evaporation of the water, and is subsequently fed into the reactor again. In the process according to the invention, the partial stream of reaction mixture which is removed per hour can amount to 0.01 to 30 times, preferably 0.05 to 20 times, most preferably 0.1 to 10 times the reactor content.

In another embodiment, the water can be removed by spontaneous evaporation during depressurisation down to a reduced pressure. In the course of this procedure the partial stream which is removed is cooled and has to be reheated to the reaction temperature before being recycled.

In a further embodiment, a distillation column can be employed for the removal of water, as described in JP-04 257 546.

The water formed in the reaction is preferably removed by stripping with excess reaction gas. The amount of reaction gas used in this respect is 1 to 100,000 Nl per liter of reaction mixture, preferably 5 to 50,000 Nl per liter of reaction mixture, most preferably 10 to 10,000 Nl per liter of reaction mixture.

The reaction gas in the process according to the invention consists of carbon monoxide, oxygen, and optionally of an inert gas.

The proportion of carbon monoxide and oxygen in the reaction gas can be varied within broad concentration limits, but a $CO:O_2$ molar ratio (normalised to CO) from 1:0.001 to 1:0.5, preferably 1:0.01 to 1:0.4, and most preferably from 1:0.02 to 1:0.3, is advisedly set. At these molar ratios the oxygen partial pressure is high enough to be able to achieve high space-time yields. The reaction gases are not subject to any particular purity requirements. Thus synthesis gas can be employed as the CO source and air can be employed as the $O_2$ carrier. However, it should be ensured that no catalyst poisons such as sulphur or compounds thereof are introduced. In a preferred embodiment of the process according to the invention, pure CO and pure oxygen are used.

The inert constituents of the reaction gas in the process according to the invention may be nitrogen, carbon dioxide or noble gases, and may also be organic compounds which are stable under the reaction conditions and which optionally form an azeotrope with water. The concentration of inert gas in the reaction gas is 0 to 60% by volume, preferably 0 to 20% by volume, most preferably 0 to 5% by volume.

Examples of aromatic hydroxy compounds which can be reacted according to the invention include phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A; phenol is preferred. Aromatic hydroxy compounds which can be used according to the invention may be singly- or doubly-substituted with $C_1$–$C_4$ alkyl, $C_1$–$C_4$ alkoxy, fluorine, chlorine or bromine.

Both organic and inorganic bases or mixtures of the same can be used in the process according to the invention. Examples of inorganic bases include alkali metal hydroxides and carbonates, and alkali metal carboxylates or other salts of weak acids, as well as alkali salts of aromatic hydroxy compounds of formula (II), e.g. alkali metal phenolates. Hydrates of alkali metal phenolates can also be used in the process according to the invention. Sodium phenolate trihydrate can be cited as an example of a hydrate such as this. However, the amount of water added is preferably calculated so that a maximum of 5 moles of water are used per mole of base. In general, higher concentrations of water result in poorer conversions and in the decomposition of the carbonates formed. Examples of organic bases include tertiary amines, which may contain $C_6$ to $C_{10}$ aryl radicals, $C_7$ to $C_{12}$ aralkyl radicals and/or $C_1$ to $C_{20}$ alkyl radicals as organic radicals, pyridine bases and hydrogenated pyridine bases. The following can be cited as examples: triethylamine, tripropylamine, tributylamine, trioctylamine, benzyldimethylamine, dioctylbenzylamine, dimethylphenethylamine, 1-dimethylamino-2-phenylpropane, pyridine, N-methylpyridine, 1,2,2,6,6-pentamethylpiperidine, or nitrogen bases such as amidines, e.g. DBU (1,8-diazabicyclo[5.4.0]undec-7-ene) and DBN (1,5-diazabicyclo[4.3.0]non-5-ene), or guanidines such as TBD (1,5,7-triazabicyclo[4.4.0]dec-5-ene). An alkali salt of an aromatic hydroxy compound is preferably used as a base, most preferably an alkali salt of the aromatic hydroxy compound which is also to be reacted to form the organic carbonate. These alkali salts may be lithium, sodium, potassium, rubidium or caesium salts. Lithium, sodium and potassium phenolates are preferred; sodium phenolate is particularly preferred.

The amount of base used is 0.01 to 20% by weight with respect to the weight of the reaction mixture. This amount is preferably 0.05 to 15% by weight, most preferably 0.1 to 5% by weight.

The base can be added to the reaction mixture as a pure compound in solid form or as a melt. In a further embodiment of the invention, the base is added to the reaction mixture as a solution which contains 0.1 to 80% by weight, preferably 0.5 to 65% by weight, most preferably 1 to 50% by weight, of the base. Both alcohols and phenols, such as the phenol to be reacted for example, and inert solvents can be used as solvents here. Examples of suitable solvents include dimethylacetamide, N-methylpyrrolidone, dioxane, t-butanol, cumyl alcohol, isoamyl alcohol, tetramethylurea, diethylene glycol, halogenated hydrocarbons (e.g. chlorobenzene or dichlorobenzene) and ether. These solvents can be used on their own or in any combination with each other. Thus one embodiment of the process according to the invention consists of dissolving the base in a phenol melt which has been diluted with a solvent. The base is preferably dissolved in the melt of an aromatic hydroxy compound, more preferably in a melt of the aromatic hydroxy compound which is to be reacted to form the organic carbonate. The base is most preferably added dissolved in phenol.

The ratio of base to platinum metal, e.g. palladium, is preferably selected so that 0.1 to 500, preferably 0.3 to 200, most preferably 0.9 to 130, equivalents of base are used per mole of platinum metal.

The process according to the invention is preferably conducted without a solvent. Inert solvents can also be used, however. Suitable examples include dimethylacetamide, N-methylpyrrolidone, dioxane, t-butanol, cumyl alcohol, isoamyl alcohol, tetramethylurea, diethylene glycol, halogenated hydrocarbons (e.g. chlorobenzene or dichlorobenzene) and ether.

The platinum metal catalysts which are suitable for the process according to the invention consist of at least one metal of Group VIII, preferably palladium. The catalyst can be added in various forms in the process according to the invention. Palladium can be used in metallic form or in the form of palladium compounds of oxidation states 0 and +2, for example as palladium(II) acetylacetonate, as a halide, as a carboxylate of $C_2$–$C_6$ carboxylic acids, as a nitrate, as an oxide or in the form of complex compounds, which may contain carbon monoxide, olefines, amines, phosphines and halides for example. Palladium bromide and palladium acetylacetonate are particularly preferred.

The amount of platinum metal catalyst used in the process according to the invention is not restricted. The amount of catalyst used is preferably such that the concentration of the metal in the reaction batch is 1–3000 ppm, most preferably 5–500 ppm.

A metal of Groups III B, IV B, V B, VI B, VII B, VIII B, I B or II B (CAS nomenclature) is used as a co-catalyst for the process according to the invention, wherein the metal can be used in various oxidation states. Suitable examples include manganese(II), manganese(III), copper(I), copper (II), cobalt (II), cobalt(III), vanadium(III) and vanadium (IV). The metals can be used as halides, as oxides, as carboxylates of $C_2$–$C_6$ carboxylic acids, as diketonates or as nitrates, for example, or as complex compounds which may contain carbon monoxide, olefines, amines, phosphines and halides, for example. Manganese compounds are preferably used in the process according to the invention, more preferably complexes of manganese(II) and manganese(III), most preferably manganese(II) acetylacetonate and manganese(III) acetylacetonate.

The co-catalyst is used in an amount such that the proportion thereof in the reaction mixture is 0.0001 to 20% by weight, preferably 0.005 to 5% by weight, most preferably 0.01 to 2% by weight.

Examples of quaternary salts which are used according to the invention include ammonium, phosphonium or sulphonium salts which are substituted with organic radicals. Ammonium, phosphonium and sulphonium salts are suitable which contain $C_6$ to $C_{10}$ aryl radicals, $C_7$ to $C_{12}$ aralkyl radicals and/or $C_1$ to $C_{20}$ alkyl radicals as organic radicals and which contain a halide, tetrafluoroborate or hexafluorophosphate as the anion. Ammonium salts which contain $C_6$ to $C_{10}$ aryl, $C_7$ to $C_{12}$ aralkyl and/or $C_1$ to $C_{20}$ alkyl radicals as organic radicals and which contain a halide as the anion are preferably used. Tetrabutylammonium bromide is particularly preferred. The amount of a quaternary salt such as this is 0.1 to 20% by weight of the reaction mixture, preferably 0.5–15% by weight, most preferably 1–5% by weight.

The platinum metal catalyst is activated before use in the process according to the invention. For this purpose the platinum metal compound, the amount of which in the process according to the invention is not restricted but which is preferably calculated so that the concentration of the platinum metal in the activation batch is 0.0001 to 30% by weight, most preferably 0.001 to 10% by weight, is dissolved in an inert solvent or directly in the melt of the organic hydroxy compound or mixtures of the same. A quaternary salt from the group comprising the compounds described above is added to this solution. This solution is subsequently treated with carbon monoxide at 15° to 200° C., preferably at 20° to 150° C., most preferably at 40° to 100° C. This can be effected either by passing in carbon monoxide at normal pressure in an amount of 0.1 to 250 l/hour, preferably 0.5 to 200 l/hour, most preferably 1 to 100 l/hour per gram of platinum metal used, or can also be effected by treating the solution with carbon monoxide in an autoclave under a pressure of 1 to 300 bar, preferably 1 to 200 bar, most preferably 1 to 150 bar. The time of activation depends on the platinum metal catalyst used and on the inert solvent which is optionally used. In general, it ranges from a few minutes to a few hours. The platinum metal catalyst can be activated immediately before the reaction, but can also be isolated and stored after separating the solvent or the organic hydroxy compound, e.g. by distillation.

In a further preferred embodiment, heterogeneous catalysts, in which the platinum metal and optionally the co-catalyst also are deposited on a support, are used as powders or moulded bodies instead of the homogeneous catalyst system. The remaining components of the catalyst system are homogeneously dissolved in the reaction mixture. The amount of platinum metal to the total weight of the heterogenous catalyst is 0.01 to 15% by weight, preferably 0.05 to 10% by weight, calculated as platinum metal.

At least one metallic compound of Groups IIIB, IVB, VB, VIB, VIIB, VIIIB, IB or IIB of the periodic table of the elements (CAS notation) or of the rare earth elements (atomic numbers 58-71) is used as a co-catalyst on the catalyst support. Compounds of Mn, Cu, Co, V, Zn, Ce and Mo are preferably used; compounds of Mn, Co, Cu, Mo and Ce are most preferably used.

The amount of compound containing the co-catalyst, in the state in which it is ready for reaction, is 0.01 to 15% by weight, preferably 0.05 to 10% by weight, calculated as the metal and with respect to the total weight of the heterogeneous catalyst.

Suitable catalyst supports include one or more metal oxides from the group comprising V, Mn, Ti, Cu, Zr, La and the rare earth metals (atomic numbers 58-71), both in the sense of chemically homogeneous pure substances and in admixture, and also include iron and cobalt oxides, and nickel, aluminium, silicon and magnesium oxides, zeolites and activated carbons. If the supported catalyst is used as a powder, the stirred vessels to be used for mixing the reaction components are equipped with stirrers which can be used for this purpose, or are fashioned as bubble column reactors.

When employing supported catalyst powders as a suspension in stirred vessels or bubble columns, amounts of 0.001 to 50% by weight, preferably 0.01 to 20% by weight, most preferably 0.1 to 10% by weight of supported catalyst powder are used with respect to the amount of reaction mixture used.

In particularly preferred embodiments, the heterogeneous supported catalysts are used as fixed catalysts in stirred vessels, in bubble columns, in a trickling phase reactor or in cascades of these reactors. Separation of the supported catalyst is then dispensed with completely.

Stirred vessels, autoclaves, distillation columns and bubble columns are suitable as reactors for the process according to the invention with a homogeneous or heterogeneous catalyst, and when fixed heterogeneous catalysts are employed, trickling phase reactors are also suitable, and can be used as single reactors or as a cascade.

2 to 15, preferably 2 to 10, most preferably 2 to 5 reactors can be connected in series in a cascade.

The reaction gas can be fed in counter-current or co-current to the liquid stream in the single reactor or in cascade reactors. CO and oxygen can be metered in jointly or separately from each other, and the amount and composition of the gas can also be different for the individual reactors of a cascade. It may possibly be advantageous to effect spatial separation of the feed points of CO, oxygen and optionally of inert gas in a single reactor or in the reactors of a cascade.

In order to mix the reaction components in stirred vessels the latter are fitted with stirrers which are suitable for this purpose. Stirrers such as these are known to one skilled in the art. Suitable examples include: disc, impeller, propeller, blade, MIG and Intermig stirrers, tube stirrers and various types of hollow stirrers. The preferred stirrers are those which permit the effective mixing of gases and liquids, for example hollow tube sparging stirrers, propeller stirrers, etc.

The following types of bubble columns can be used in the process according to the invention: simple bubble columns, bubble columns with built-in parts, e.g. bubble columns with parallel chambers, bubble column cascades with sieve bottoms or perforated bottoms, bubble columns with packings, with static mixers, pulsating sieve bottom bubble columns, loop-type bubble column reactors such as airlift loop-type bubble column reactors, downflow loop-type bubble column reactors, jet and loop-type bubble column reactors, open jet reactors, jet nozzle reactors, bubble columns with liquid hold-up jets, downflow-upflow bubble columns, and other bubble column reactors known to one skilled in the art (Chem. Ing. Tech. 61 (1979) 208; W.-D. Deckwer: Reaktionstechnik in Blasensaulen, Otto Salle Verlag 1985).

In one preferred embodiment, bubble column reactors and bubble column cascades are used which permit the effective mixing of gas and liquids, such as cascade bubble columns and loop-type bubble column reactors for example.

In order to maintain good, thorough mixing of the liquid and the reaction gas, distributing and redispersion elements may be provided along the longitudinal axis of bubble column reactors. Single hole plates, perforated plates, sieve bottoms and other built-in parts known to one skilled in the art are used as fixed redispersion elements.

Customary devices such as porous sintered plates, perforated plates, sieve bottoms, insertion tubes, nozzles, sparging rings and other dispersing devices known to one skilled in the art can be used for the primary dispersion of the reaction gas in the liquid phase during the metered addition of the gas.

The process according to the invention can be put into effect in various design variants. One possibility consists of carrying it out batch-wise. In this procedure, CO and oxygen are passed into the reaction mixture either through a sparging stirrer in the case of a stirred vessel, or via other known gas distribution elements. After the optimum conversion has been achieved, the reaction mixture is removed from the reactor or is optionally worked up in the reactor.

Supported catalysts in powder form can be separated from the reaction mixture by filtration, sedimentation or centrifuging, for example.

Supported catalysts which are used in batch operations can optionally be reused without purification when the same starting materials are used. In a continuous mode of operation the supported catalysts which are used can remain in the reactor for a long time and can optionally be regenerated.

In a preferred embodiment of the process according to the invention, a continuous mode of operation is employed in a single reactor or in a cascade of reactors. When heterogeneous fixed catalysts are used, they can remain in the reactor for a long time and can optionally also be regenerated there. In this variant of the process according to the invention, a part of the reaction mixture corresponding to the feed streams is continuously removed, with the level in the reactor being kept constant, the diaryl carbonate formed in the reactor is isolated from this part of the reaction mixture in a manner which is known in principle, e.g. by fractional crystallisation of the melt (EP-A 687 666) or by an extraction method, and the mixture which is depleted in diaryl carbonate is subsequently recycled to the process. The part of the reaction mixture which is removed is optionally treated in addition with diaryl carbonate before the isolation of the diaryl carbonate, so that the mixture contains at least 40% by weight of diaryl carbonate. Work-up is thereby made easier.

The following examples illustrate the method according to the invention without restricting it thereto.

EXAMPLES

Example 1: (21.4% DPC addition)

0.12 g palladium bromide and 11.64 g tetrabutylammonium bromide were dissolved at 60° C. in 150 g DPC and 500 g phenol in an autoclave (1 liter) fitted with a sparging stirrer, a bulwark, means for the continuous introduction of gas, a pressure maintenance device, a condenser and downstream cold traps. Carbon monoxide (25 l/hour) was passed through this solution for one hour in order to activate the catalyst. 1.078 g manganese(III) acetylacetonate and 2.12 g sodium phenolate dissolved in 50 g phenol were then added, and the pressure was adjusted to 10 bar and the reactor temperature was raised to 80° C. whilst passing in a gas mixture of carbon monoxide and oxygen (96.5:3.5% by volume). The amount of gas mixture, consisting of carbon monoxide and oxygen, was adjusted to 280 Nl/hour. A sample was taken from the reaction mixture every hour and was analysed by gas chromatography. The analyses showed that the reaction mixture contained 30.1% by weight diphenyl carbonate after one hour, 38.5% by weight diphenyl carbonate after 2 hours, and 46.0% by weight diphenyl carbonate after 3 hours. 16.7 g of a phenol/water mixture condensed in the cold traps.

The phenol selectivity was high and constant at >99%. No by-products from a DPC secondary reaction were observed, and larger amounts of $CO_2$ resulting from the hydrolysis of DPC were not observed.

Example 2: (35.7% DPC addition)

0.12 g palladium bromide and 11.64 g tetrabutylammonium bromide were dissolved at 60° C. in 250 g DPC and 400 g phenol in an autoclave (1 liter) fitted with a sparging stirrer, a bulwark, means for the continuous introduction of gas, a pressure maintenance device, a condenser and downstream cold traps. Carbon monoxide (25 l/hour) was passed through this solution for one hour in order to activate the catalyst. 1.078 g manganese(III) acetylacetonate and 2.71 g potassium phenolate dissolved in 50 g phenol were then added, and the pressure was adjusted to 9 bar and the reactor temperature was raised to 85° C. whilst passing in a gas mixture of carbon monoxide and oxygen (96.5:3.5% by volume). The amount of gas mixture, consisting of carbon monoxide and oxygen, was adjusted to 320 Nl/hour. A sample was taken from the reaction mixture every hour and was analysed by gas chromatography. The analyses showed that the reaction mixture contained 43.9% by weight diphenyl carbonate after one hour, 51.9% by weight diphenyl carbonate after 2 hours, and 59.8% by weight diphenyl carbonate after 3 hours. 17.8 g of a phenol/water mixture condensed in the cold traps.

The phenol selectivity was high and constant at >99%. No by-products from a DPC secondary reaction were observed, and larger amounts of $CO_2$ resulting from the hydrolysis of DPC were not observed.

Example 3: (50% DPC addition)

0.16 g palladium bromide and 11.64 g tetrabutylammonium bromide were dissolved at 60° C. in 350 g DPC and 300 g phenol in an autoclave (1 liter) fitted with a sparging stirrer, a bulwark, means for the continuous introduction of gas, a pressure maintenance device, a condenser and downstream cold traps. Carbon monoxide (25 l/hour) was passed through this solution for one hour in order to activate the catalyst. 1.078 g manganese(III) acetylacetonate and 2.115 g sodium phenolate dissolved in 50 g phenol were then added, and the pressure was adjusted to 12 bar and the reactor temperature was raised to 90° C. whilst passing in a gas mixture of carbon monoxide and oxygen (96.5:3.5% by volume). The amount of gas mixture, consisting of carbon monoxide and oxygen, was adjusted to 400 Nl/hour. A sample was taken from the reaction mixture every hour and was analysed by gas chromatography. The analyses showed that the reaction mixture contained 58.1% by weight diphenyl carbonate after one hour, 66.0% by weight diphenyl carbonate after 2 hours, and 73.8% by weight diphenyl carbonate after 3 hours. 10.4 g of a phenol/water mixture condensed in the cold traps.

Example 4:

Coating powdered titanium dioxide with palladium and manganese:

300 ml of a solution of 40.5 g (0.16 mole) manganese(II) nitrate tetrahydrate in water was added at room temperature to a slurry of 283.5 g titanium dioxide powder (manufacturer: Norton) in 1500 ml water. The mixture was then made alkaline with dilute sodium hydroxide solution. The suspension was filtered off under suction, washed with water, dried at 100° C. and calcined for 3 hours at 300° C. The manganese-doped support was slurried in 1500 ml water and treated with 300 ml of a solution containing 50 g sodium tetrachloropalladate(II) solution comprising 15% by weight of palladium. The mixture was then made alkaline with dilute sodium hydroxide solution. The suspension was filtered off under suction, washed, and dried at 100° C.

The catalyst contained 2.5% by weight Pd and 3% by weight Mn, calculated as the metal in each case.

Use of the supported catalyst for the production of diphenyl carbonate:

Example 1 was repeated, except that, instead of 0.12 g palladium bromide, 2 g of the heterogeneous catalyst prepared as above was used in suspension and a pressure of 8 bar was employed.

The analyses showed that the reaction mixture contained 28.3% by weight diphenyl carbonate after one hour, 35.1% by weight diphenyl carbonate after 2 hours, and 41.8% by weight diphenyl carbonate after 3 hours. 21.3 g of a phenol/water mixture condensed in the cold traps.

Example 5:

A continuous test was performed using the apparatus which is schematically illustrated in FIG. 1, consisting of a 1 liter autoclave (A), means for the continuous metered addition of gas and starting materials, and means for the continuous outward transfer of gas and liquid. After depressurisation, the reaction gas flowed through three cold traps (B), in which stripped-out water and phenol condensed.

A pump conveyed the activated catalyst solution (per hour: 0.10 g palladium bromide, 8.31 g tetrabutylammonium bromide and 1.07 g manganese(III) acetylacetonate in a melt comprising 100 g DPC and 350 g phenol) into the reactor via line 1. Another pump simultaneously metered 1.511 g sodium phenolate per hour, dissolved in 50 g phenol, into the reactor via line 2.

The temperature of the reaction solutions was 80° C. 300 Nl per hour of a gas mixture consisting of carbon monoxide and oxygen (96.5:3.5% by volume) were passed into the reactor via line 3. The reactor pressure was 10 bar and the internal temperature was controlled at 80° C. Excess reaction gas left the reactor via line 4. The internal pressure of the reactor was held constant via a pressure transducer and a control valve in line 4.

About 500 g per hour of the reaction mixture were removed from the reactor via line 5, by means of a pump, and were fed to the diphenyl carbonate isolation stage. A sample was taken hourly from the reaction mixture which had been transferred out and was analysed by gas chromatography. After about 5 hours, the apparatus was in equilibrium. The analyses showed that the reaction mixtures contained 28.2% by weight diphenyl carbonate. The phenol selectivity was high and constant at >99%.

No by-products from a DPC secondary reaction were observed, nor were larger amounts of $CO_2$ resulting from the hydrolysis of DPC.

Example 6:

The procedure was as in Example 5, except that 0.10 g palladium bromide, 8.31 g tetrabutylammonium bromide and 1.07 g manganese(III) acetylacetonate in a mixture comprising 250 g DPC and 200 g phenol were fed into the reactor per hour.

A sample was taken hourly from the reaction mixture which had been transferred out and was analysed by gas chromatography. After about 5 hours, the apparatus was in equilibrium. The analyses showed that the reaction mixtures contained 58.7% by weight diphenyl carbonate. The phenol selectivity was high and constant at >99%.

No by-products from a DPC secondary reaction were observed, nor were larger amounts of $CO_2$ resulting from the hydrolysis of DPC.

Before it entered the DPC isolation stage, the DPC content of the reaction mixture was increased to about 71% by weight DPC by the subsequent addition of 225 g DPC.

The DPC was isolated according to EP-A 687 666 by fractional crystallisation of the melt in a tubular crystalliser.

The reaction mixture was introduced into a vertical jacketed tube of height 100 cm and about 3 cm inside diameter and was cooled at 2° C./hour from 75° C. At 68° C. the melt was seeded with a few crystals of diphenyl carbonate. As the melt reached 55° C., it was allowed to drain out. The heating medium was subsequently heated at 2° C./hour again. After reaching 69° C., the crystalline mass which remained in the tube melted out and was captured separately. It contained 92% by weight DPC. The 437 g of melt as a whole which had previously been separated consisted of 57.2% by weight of diphenyl carbonate. The crystalline material was subsequently freed from residual phenol by distillation.

We claim:

1. A process for producing diaryl carbonate of the formula

$$R-O-CO-O-R \qquad (I)$$

wherein

R represents a substituted or unsubstituted $C_6$–$C_{12}$ aryl which comprises reacting an aromatic hydroxy compound of the formula

$$R-O-H \qquad (II)$$

wherein

R has the meaning given above,
with carbon monoxide and oxygen in the presence of a platinum metal catalyst, a co-catalyst, a quaternary salt and a base at a temperature of 30° to 200° C. and at a pressure of 1 to 200 bar, wherein the reaction is conducted in a melt comprising said diaryl carbonate and said aromatic hydroxy compound, which at the start of the reaction is provided with a content of said diaryl carbonate of at least 20% by weight, and isolating diaryl carbonate from the melt.

2. A process according to claim 1, wherein additional of said diaryl carbonate is added to the melt before isolating the diaryl carbonate.

3. A process according to claim 1, wherein part of the reaction mixture is continuously removed, diaryl carbonate is isolated from the removed part, and the part is recycled to the process.

4. A process according to claim 3, wherein the part of the reaction mixture which is removed is treated with said diaryl carbonate before the isolation of the diaryl carbonate.

5. A process according to claim 1, wherein R in the diaryl carbonate of formula (I) is substituted or unsubstituted phenyl.

6. A process according to claim 1, wherein R in the diaryl carbonate of formula(I) is unsubstituted phenyl.

7. The process of claim 1, wherein the reaction is provided with at lest 30% by weight of said diaryl carbonate at the start of the reaction.

8. The process of claim 1, wherein the reaction is provided with at least 40% by weight of said diaryl carbonate at the start of the reaction.

* * * * *